United States Patent [19]

Martin

[11] Patent Number: 6,016,203
[45] Date of Patent: Jan. 18, 2000

[54] GAS SENSOR

[76] Inventor: Hans Göran Evald Martin, Östansjö 2837, 820 60 Delsbo, Sweden

[21] Appl. No.: 09/051,852

[22] PCT Filed: Nov. 11, 1996

[86] PCT No.: PCT/SE96/01448

§ 371 Date: Apr. 22, 1998

§ 102(e) Date: Apr. 22, 1998

[87] PCT Pub. No.: WO97/18460

PCT Pub. Date: May 22, 1997

[30] Foreign Application Priority Data

Nov. 13, 1995 [SE] Sweden ................................ 9504020

[51] Int. Cl.[7] .................................................. G01N 21/00
[52] U.S. Cl. ........................... 356/432; 356/437; 356/442
[58] Field of Search .................................... 356/437, 432, 356/433, 442

[56] References Cited

U.S. PATENT DOCUMENTS

| | | |
|---|---|---|
| 4,756,622 | 7/1988 | Wong . |
| 5,060,508 | 10/1991 | Wong . |
| 5,163,332 | 11/1992 | Wong . |
| 5,340,986 | 8/1994 | Wong . |
| 5,488,227 | 1/1996 | Sweet . |
| 5,550,375 | 8/1996 | Peters et al. . |

FOREIGN PATENT DOCUMENTS

| | | |
|---|---|---|
| 0647845 A1 | 4/1995 | European Pat. Off. . |
| 0704691 A2 | 4/1996 | European Pat. Off. . |

OTHER PUBLICATIONS

White, John U., "Long Optical Paths of Large Aperture", J.O.S.A., vol. 32, May, 1942, pp. 285–288.

*Primary Examiner*—Frank G. Font
*Assistant Examiner*—Reginald A. Ratliff
*Attorney, Agent, or Firm*—Burns, Doane, Swecker & Mathis, L.L.P.

[57] ABSTRACT

The invention comprises a gas sensor (1), designed to enable a measurement of a gas sample that is enclosed in a cavity (2), having the shape of a block (50); the wall or wall sections of the cavity exhibiting highly-reflective properties for light. Said cavity contains means (51) for incoming rays of light, and means (52) for outgoing rays of light. Said cavity (2) exhibits opposing surface sections (55a, 56a, 57a) that are designed and coordinated so that the incoming rays of light (60) are arranged to pass—without reflecting, or without appreciably reflecting within a plane (the x-z plane)—across said cavity (2) to a concave mirror surface (55a) that is oriented in a right angle to the plane; that said rays of light are arranged to pass reflected across said cavity (2) in a plane of the mirror surface to the other surfaces (56a, 57a), thereby forming a measuring path before the reflected beams of light are aimed towards said means (52) for exiting light.

18 Claims, 2 Drawing Sheets

GAS SENSOR

TECHNICAL FIELD

The present invention relates to a gas cell and/or to a gas sensor.

By gas cell we mean a cavity in which a gas sample exists, which gas sample is penetrated by a beam of light or by rays of light, to enable an analysis of the gas structure and concentration by means of the change of the spectrum of the penetrating beam of light, by means of a light source and/or a light detector, which are positioned outside of the cavity, or the unit in which the cavity is formed.

If the unit is permitted to contain said light source, light detector, and/or circuits for evaluating gas structures and/or gas concentrations, then it is called a gas sensor.

For the sake of simplicity, the description that follows and the Claims section use the expression gas sensor for both types of design.

In particular, the present invention relates to a gas sensor that is designed to enable a measurement of a gas sample enclosed in a cavity.

According to the invention, the design of the gas sensor comprises a block, which contains a cavity that serves as a gas cell. As relates to light, the wall or wall sections of the cavity exhibit highly-reflective properties.

Said cavity contains means, such as an opening or section for incoming rays of light or light, and means, such as an opening or section for rays of light or light to be received within or exit the cavity after the light has been reflected one or more times inside the cavity.

In particular, the present invention provides a gas sensor, which is part of a system wherein a gas and/or a portion of gas in a gas sample is analysed with respect to the gas itself and/or to the proportional share (concentration) of the gas in the sample, using an absorption spectrum, which appears in the light spectrum of the exiting light.

To better understand the present invention and its characteristics, we are required to use expressions such as directly-reflected light beam or rays of light, and indirectly-reflected light beam or rays of light.

By directly-reflected light beam or rays of light we mean that a beam of light may pass through the cavity without reflecting in the cavity's delimiting parallel surface sections, except in a mirror surface opposite the beam of light, which reflects the beam of light in the same plane, but in a different direction.

By indirectly-reflected light beam or rays of light we mean that a beam of light may pass through the cavity reflecting one or more times in the mirror structure of the cavity's delimiting surface sections.

BACKGROUND ART

Gas sensors of the kind described above exist in various different embodiments.

These kinds of gas sensors have a cavity or space that functions as a gas cell through which rays of light are allowed to pass. Interacting with the gas cell are light emitting means and light receiving means (light receiver). The light receiver is designed to enable an evaluation of the current lines of absorption in the light spectrum for an exiting beam of light, or rays of light.

Within the cavity, between the light emitting means and the light receiver in the gas cell, is a light path, hereafter called a measuring path or optical measuring path.

In optical applications the terms "geometrical path" and "optical path" are sometimes used, where the geometrical path is a geometrical distance and the optical path is a geometrical distance multiplied with the refractive index of the medium through which the light passes. In so called "standard air", where the refractive index is 1, the optical path is thus equal to the geometrical path.

The terms "measuring path" and "optical measuring path" are used synonymously in this description since the gas concentrations at hand are very low which gives a refractive index very close to 1.

Even if the refractive index would deviate substantially from 1, for example at a measurement of a fluid, these terms could be used synonymously since the used technique is based on reflections of light in a homogeneous medium and not on transmissions of light through various mediums with different refractive indexes, wherefore the compensations for variations in the refractive index is not required. It is nevertheless obvious for a person skilled in the art what measures are required if the light emitting means and/or the light receiving means are positioned in an optical medium that differs in refractive index from the medium inside the gas cell.

It is also known that thorough analysis of gas type, gas mixture, and/or gas concentration in a gas sensor with a gas cell is based on the following relationship: when concentrations are low, and when the absorption spectrum for a given gas is not expressly obvious, then a long measuring path is required for a light beam that passes through a gas sample in order to achieve an accurate result.

Today, a measuring path of approximately 0.1 meters is required in most practical applications that use current technology to produce beams of light, to detect and receive beams of light after they have been reflected a given number of times, and to analyse the absorption spectrum for the beam of light.

The U.S. Pat. No. 5,163,332 shows and describes a gas sensor that can be used to analyse gases. The gas sensor consists of a long, hole-shaped pipe with internal light reflective surfaces that allow the pipe to function as a channel or conductor of light, thereby creating a measuring path for transferring beams of light from a light source to a defector, and through a gas sample enclosed in the pipe.

The beams from the light source are arranged to be indirectly reflected by opposing surfaces—that is, by indirect reflection in all directions.

By reflection in all directions in an optical conductor, we mean that if rays of light, coordinated into a beam of light with diverging beams are allowed to enter a pipe whose inside has light-reflective properties, then the beams of light that angle away from the centre line, the z-axis, will be reflected in the x-z plane as well as in the y-z plane.

Further, several openings in the wall section of the pipe are shown equipped with filters, which permit a gas sample to freely be introduced into the pipe, or to freely exit from inside it.

Attempts have been made to reduce the external dimensions of a gas sensor or gas cell while obtaining a long measuring path.

The following publications are referred to as examples of the background art.

The U.S. Pat. No. 5,340,986 showed a diffusion type gas sensor, where the required length for the gas cell can be reduced by half, relative to a desired measuring path, by arranging a transmitter and a receiver in one end of the pipe, and a mirror in the other end of the pipe, as well as by giving the inside of the pipe light-reflective properties.

This method offers a directly-reflected light beam and indirectly-reflected rays of light.

The U.S. Pat. No. 5,060,508 made known a gas cell with an extended measuring path—relative to its external dimensions—shaped in a block with small external dimensions. The block is equipped with several canal sections, oriented at the front and back, and connected to one another. The walls for these connected canal sections are coated with a highly-reflective agent, causing the resultant passage to serve as an optical conductor, in order to transfer beams of light by means of indirect reflection in all directions. Several minor passages permit the gas in an area surrounding the pipe to diffuse into the passage.

In this example, the gas cell is created by positioning the two block halves against one another. These halves can be cast of plastic, making them relatively inexpensive to produce.

The content of the publication EP-A1-0 647 845 is also a part of the background art in this regard.

Considering the characteristics exhibited in the present invention, we should also mention that an absorption cell was previously made known by J. U. White, in the Journal of Optical Society of America, Vol. 32, page 285 (1942). A cell was shown and described, consisting of three spherically concave mirrors, each of which had the same radius of curvature, and was positioned to create a desired optical measuring path.

The cell was developed in order to obtain an extended measuring path for a directly-reflected beam of light in a gas sensor. By applying the principles described in the above-mentioned publication, it has been possible to develop gas sensors whose optical measuring paths exceed 10 meters in length.

Through this example, it is known to position the mirrors far apart, ordinarily 0.3 to 3 meters, and adjust the rays of light so that their diverging angle is very slight.

Further, the rays of light produced must not be interfered with by indirect collateral reflections. Instead, they must be reflected directly between the mirrors.

The U.S. Pat. No. 4,756,622 describes how other measures have been taken to create a long measuring path for wave length absorption in gas. For example, this publication explains that the light beam may wander through a limited volume of gas very many times; for example in the order of thousands of times.

The light beam is introduced to a closed optical loop, where it is allowed to circulate through the gas sample. Then, after having circulated through the gas sample a predetermined number of times, the light is deflected from the closed optical loop by means of polarising wave conductors.

Even when the reflective factor is as high as 0.998, after 100 reflections the intensity of the light is only 80% of its original brightness. After 300 reflections, it is only approximately 50% of its original brightness.

DISCLOSURE OF THE PRESENT INVENTION

Technical Problems

Given the background art, as it has been described above, allowing that some gases may exhibit a weak tendency towards absorption, so that they can be analysed only after rays of light are brought to pass through a relatively long optical measuring path through the gas; and/or allowing for other situations in which the analysed gas may exhibit a distinct tendency towards absorption, but must be detected in very low concentrations—typically in parts per million (ppm) or less—thereby requiring a long measuring path, it ought to be considered a technical problem to be able to miniaturise the gas cell, by simple means, while at the same time providing an adapted and chosen measuring path and/or measuring paths.

Another technical problem is in being able to create a gas cell and/or a gas sensor that can be developed as an inexpensive mass-producible unit.

Another technical problem is in being able to provide a gas sensor that is so easily adjusted that it can reliably analyse poisonous gases (such as carbon monoxide, ozone, nitrogen oxide, and so on) with a detection of low concentrations in the range of ppm.

Another technical problem is in being able to create an inexpensive gas sensor that can function as a fire detector, being adapted to efficiently and accurately be able to analyse low concentrations of carbon dioxide and carbon monoxide.

Yet another technical problem is in being able to realise the measures that must be taken to create a gas cell or a gas detector through which even diverging beams of light in a first plane (for example the z-x plane) can pass without indirect (or at least appreciably-indirect) reflections directly towards a concavely bent mirror surface, while diverging beams of light in a second plane (for example the y-z plane) becomes a subject to indirect reflections between parallel mirror-structured surfaces, such as in an optical conductor.

Another technical problem is in being able to create, for a gas sensor that has successfully solved one or more of the above technical problems, conditions whereby the light detector can receive from a lens or from a concavely bent mirror directly-reflected converging beams of light with a high intensity, thereby enabling an improved analysis of gases with a weak absorption pattern and/or low concentration.

Still another technical problem is in being able to create, by simple means, conditions whereby the light detector can assess directly- and indirectly-reflected beams of light, in order to allocate indirectly-reflected beams of light a longer measuring path than directly-reflected beams of light.

Given a gas cell and/or a gas sensor of the kind describe above, another technical problem is in being able to realise the significance of adjusting and arranging, in an x-z plane, opposing light-reflecting surface sections in a cavity formed in a block, thereby enabling rays of light to pass across said cavity, without reflections (or without appreciable reflections) in said x-z plane, after which they are directly reflected a predetermined number of times in opposing concavely-bent mirror surfaces until a chosen measuring path is reached and the directly-reflected rays of light can be aimed to be received within the cavity or to pass through said opening for exiting light beams or rays of light.

If a gas sensor and/or a gas cell of the kind described above is to be miniaturised, then another technical problem is in being able to realise the significance of designing the cavity with two, ordinarily plane and parallel, light reflecting surfaces, close together, facing one another, and oriented parallel to the rays of light, creating conditions whereby incoming rays of light in a y-z plane are indirectly reflected several times before these diverging beams of light reach the concavely-bent mirror surfaces.

Another technical problem is in being able to realise the advantages and opportunities that are associated with designing at least a portion of the surface section in the x-y plane to present the shape of a grid.

Still another technical problem is in being able to realise the significance of allowing a gas sensor and/or a gas cell, in the shape of a block, to be shaped, by simple means, by applying the principles used for producing compact disks.

Another technical problem is in being able to realise the significance of, and the benefits that are associated with allowing said opposing concavely-bent surface sections to be positioned according to the principles for a White mirror.

As relates to mass production, another technical problem is in being able to create conditions whereby the opposing concavely-bent surface sections and a plane surface are shaped in a block section, while the opposite plane surface is designed in the shape of a disk, and finally, that the block section and the disk may be fastened to one another using known techniques.

Yet another technical problem is in being able to realise the significance of, and the prerequisites that are associated with, allowing opposing surface sections and said two plane surfaces to be coated with gold, and of allowing the incoming light to be chosen from within the frequency range for infrared light.

Another technical problem is in being able to provide a gas sensor and/or a gas cell that enables the use of a gas sample that can be pumped by means of a pump through the cavity, or that can be allowed to diffuse into the cavity.

Still another technical problem is in being able to show conditions for gas cells and the designed cavity, whereby the gas sample can be brought into or out of the cavity by means of recesses that lie beyond a measuring path formed for the beams light and for these purposes required light-reflecting surfaces.

Another technical problem is in being able to provide a given measurement from amongst one of several chosen measuring paths in the same cavity with a predetermined size.

Finally, it should be considered a technical problem to realise the prerequisites for being able to apportion the measuring path into a given number of segments, as well as to use the results from a measurement as a reference determination.

Solution

In order to resolve one or more of the above technical problems, the present invention is based on an earlier design for a gas sensor and/or gas cell that has been adapted to enable a measurement of a gas sample that is enclosed in a cavity, in the shape of a block; the wall or wall sections of the cavity exhibiting highly-reflective properties for light; said cavity containing means, such as an opening for incoming rays of light, and means, such as an opening, through which directly-and indirectly-reflected light may be received within or exit the cavity.

Said rays of light are arranged to pass reflected across said cavity, before the reflected beams of light are aimed to be received within the cavity or to pass through said opening for exiting light.

Given a gas sensor of this kind, the present invention shows that said cavity must exhibit opposing surface sections, arranged and coordinated so close together that incoming rays of light are arranged to be able to pass in a plane—without reflecting, or without appreciably reflecting—across said cavity towards a concavely-bent mirror surface that is oriented in a right angle to the plane.

According to the preferred embodiments that lie within the scope of invention, the cavity is formed by two light-reflecting surfaces, placed close together, facing one another in two parallel planes.

Moreover, the shape of said opposing surface sections is slightly bent.

Further, at least part of a surface section is processed to give it the shape of a grid.

Again, it is possible to allow incoming rays of light to be produced by a lamp with a narrow frequency range, and to allow the exiting rays of light to be received by a light detector with an electrical and/or an electronic circuit for analysing the present absorption spectrum.

By designing the gas sensor and/or the gas cell in the shape of a block, we are able to apply the principles that are used for producing compact disks.

Moreover, within the scope of the invention, it is possible to position opposing surface sections according to the principles for a White mirror.

In particular, the present invention shows that opposing surface sections and a plane surface have the shape of a section of a block, whereas an opposite plane surface has the shape of a disk.

The invention shows that said opposing surface sections and said two plane surfaces are coated with gold or another for light highly-reflective material. The frequency of the in-coming light is chosen to be in the range for infrared light.

According t o the invention, the gas sensor enables a gas sample to be pumped, by means of a pump, through the cavity, or the gas sensor permits a gas sample to diffuse into the cavity.

Advantages

The primary advantage that characterises a gas sensor that exhibits the significant properties of the present invention is that conditions have been created whereby it is possible to miniaturise the external dimensions of the gas sensor and/or the gas cell while at the same time creating conditions for a long, adapted measuring path whose design, which may be mass-produced inexpensively, provides acceptably high precision, in terms of measured results, by reducing the loss of reflections in at least one plane, as well as by being able to create a divergence of reflected light beams towards the light detector.

The primary characteristic features of a gas sensor, according to the present invention, are set forth in the characterising clause of Claim 1, below.

BRIEF DESCRIPTION OF THE DRAWINGS

Several exemplifying embodiments at present preferred for a gas cell and a gas sensor, having properties that are significant to the present invention, will now be described in greater detail with reference to the accompanying drawings, where.

DESCRIPTION OF PROPOSED EMBODIMENTS

Figure 1:
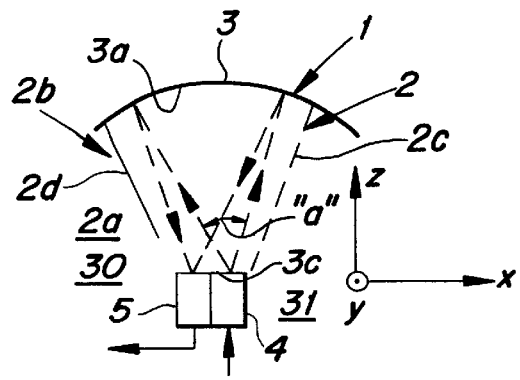
FIG. 1 shows a light emitter that sends diverging rays of light to a concave mirror surface where the rays of light converge and are reflected towards a light receiver.

FIG. 1 shows a gas sensor 1, which consists of a gas cell 2 with a concavely-bent mirror 3, bent to the shape of a partial circle and positioned in an x-y plane, with a mirror surface 3a.

The gas sensor 1 also comprises a light emitter 4 and a light receiver 5 of known design.

The light receiver 5 is connected in a known way to equipment (not pictured) in order to analyse the absorption spectrum in the received beams of light.

The vertical dimension (x-y plane) of the gas cell 2 is very small, being adapted to a selected light emitter 4 and light receiver 5. With current technology, the vertical height may realistically be between 0.1 and 0.5 mm.

With reference to FIG. 1, we see that the light emitter 4 is designed to send diverging rays of light. We assume that the angle of divergence "a" is 40°.

The true angle of divergence may vary depending on the selected light emitter and can hence be varied.

Nevertheless, the principle of the invention may be applied by collimated light or by converging rays of light, by modifying the shape of the mirror surface 3a and/or by changing the position of the light receiver.

While these embodiments will not be described in greater detail here, to a person skilled in the art, they represent common embodiments with associated modifications.

The invention is based on the principle that the portion of light rays that are oriented in the x-z plane are to pass, without reflection in the indicated side surfaces 2c and 2d and/or the plane surfaces 2a and 2b oriented in the x-z plane, to the convex mirror surface 3a, where they are directly-reflected, converging at the light detector 5.

The portion of the diverging rays of light that are oriented in the x-y plane will be able to pass—via recurring indirect reflections, in upper and lower plane surfaces 2a, 2b, to plane mirror surfaces positioned in the x-y plane—to the convex mirror surface 3a positioned in the x-y plane.

Thus, FIG. 1 indicates that diverging, cavity-delimiting surfaces 2c, 2d are also light-reflecting, contributing with indirect reflection of diverging beams of light, which diverge at an angle that slightly exceeds the angle for the surfaces 2c, 2d in the x-z plane.

The invention is based on producing beams of light from the light emitter 4, which, while diverging in the x-z plane do not reflect in the x-z plane, but are instead directly-reflected in the mirror surface 3a with no practical loss by reflection, converging at the light receiver 5 where they can be received and amplified.

The cavity 2 is delimited by the mirror surface 3a, two opposing plane mirror surfaces 2a, 2b (a lower mirror surface 2a is shown; an upper mirror surface 2b has been removed to add clarity to the drawing), and the diverging mirror surfaces 2c and 2d.

The radius of curvature for the mirror surface 3a of mirror 3 is chosen with the centre 3C in the middle, between the light emitter 4 and the light receiver 5.

A person skilled in this technique will understand that a better exchange of light is obtained when the mirror surface 3a has a slight elliptical shape with its two focal points positioned in the light emitter 4 and the light receiver 5.

It should be possible to increase the intensity of the light in the circuit of the light receiver 5, provided the mirror surface 3a is longer in its y-axis than the input window of the circuit 5; the mirror surface 3a may even be somewhat concave in the x-y plane.

Ordinarily, the cone angle "a" of the light beams is greater than 20° but less than 60°; for example, between 30° and 50°, ordinarily 40°.

Figure 2:
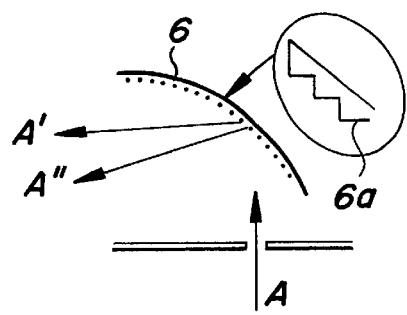
FIG. 2 shows an example of a previous design for a grid spectrometer.

FIG. 2 illustrates that a beam "A" can be aimed at a mirror or a mirror section 6 with a grid surface 6a, thereby obtaining a grid spectrometer, inasmuch as the reflected beams A' and A" from an incoming beam A have different wave lengths.

Figure 3:
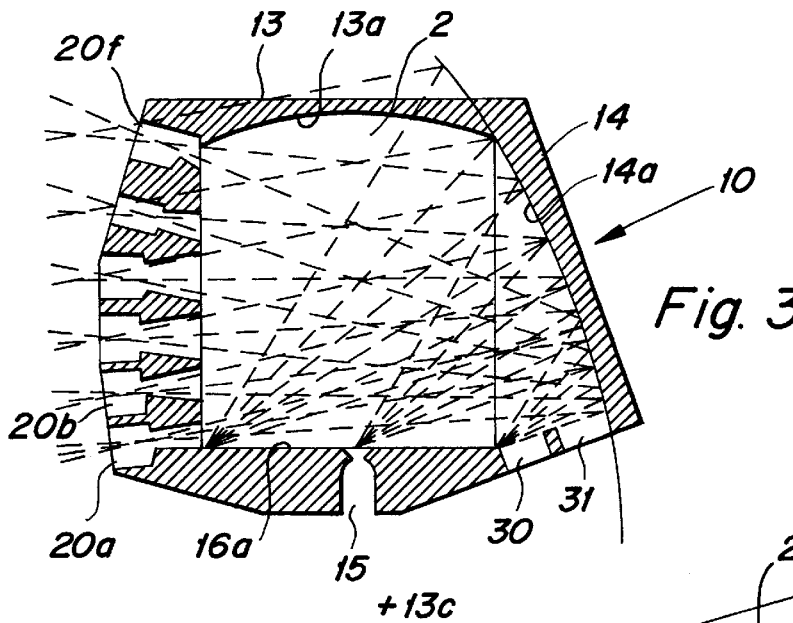
FIG. 3 shows in a plane, an embodiment of a gas cell with a built-in grid spectrometer.
Figure 4:
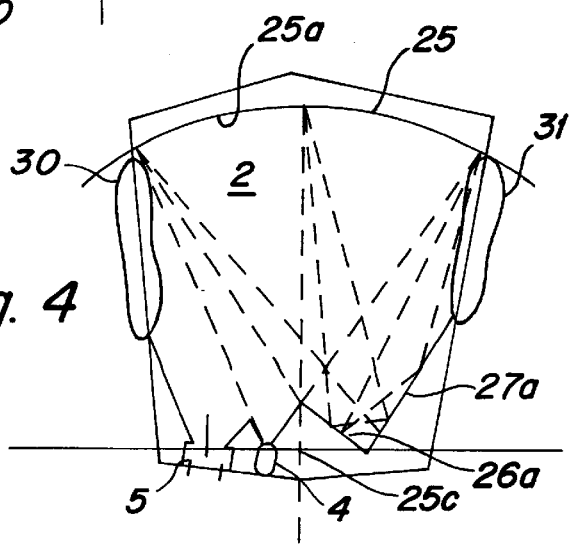
FIG. 4 shows in a plane, another embodiment with a light emitter and a light receiver positioned next to one another.
Figure 5:
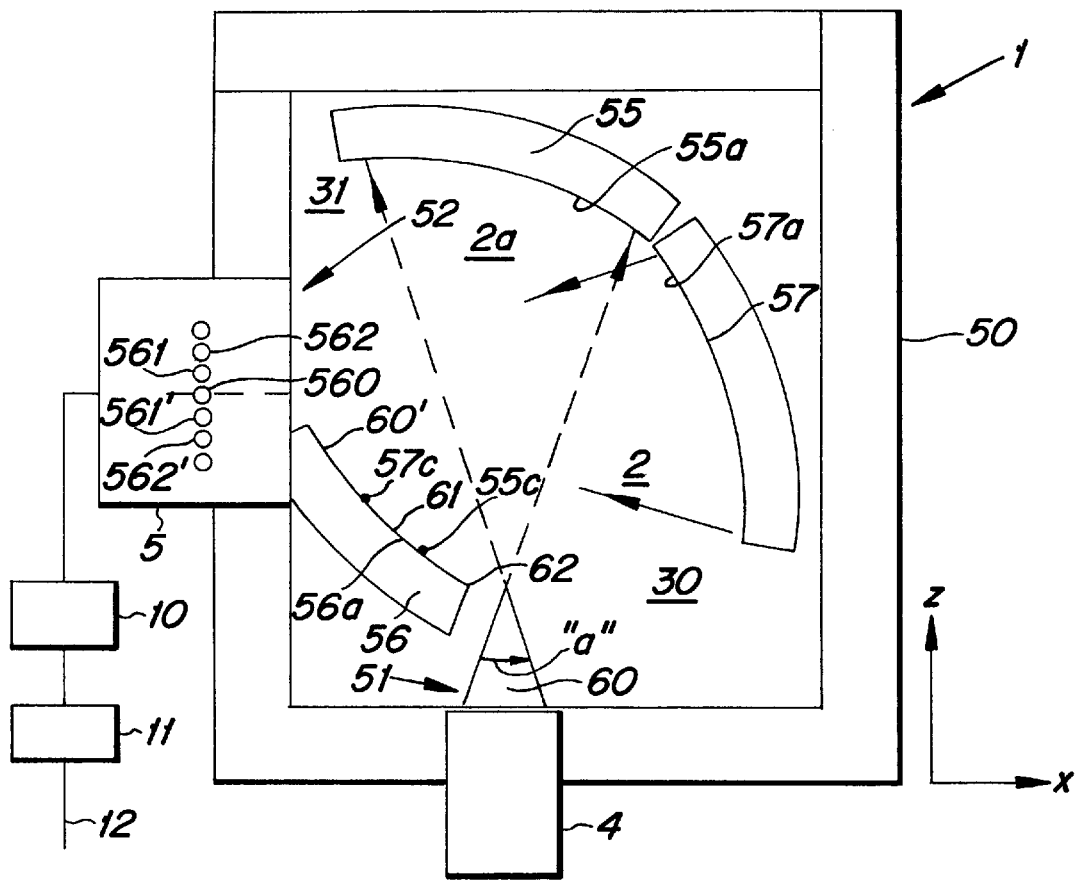
FIG. 5 shows in a plane, an embodiment that applies the principles for a White mirror.

FIGS. 3–5 show in a plane, different designs for a gas cell or a gas sensor, which exhibit the properties associated with the present invention.

Given this chosen projection, only directly-reflected light beams and rays of light are treated. The thickness of all embodiments is limited in the y-axis.

According to FIG. 3, the embodiment shows a gas sensor 10 with a gas cell whose shape is a cavity 2, having a delimited vertical dimension (y-axis), and a very broad horizontal dimension (x-z plane).

A mirror surface 13a and mirror surface 14a are angle related to one another.

The mirror surface 13a of the mirror 13 has the shape of a circular arc with a radius from point 13C.

The mirror surface 14a of the mirror 14 has the shape of a circular arc. The radial point, which is not shown, with a radius slightly exceeding that of mirror surface 13a.

When diverging rays of light are aimed into the cavity 2 through an inlet 15 by means of a source (not pictured) of diverging light rays in the opening 15, the entire mirror surface 13a is illuminated, and the light beams are reflected and collimated towards a grid surface 16a from which they are diffracted to a focusing surface 14a that reflects the focused wave length sections through openings 20a, 20b, . . . , 20f, each adapted to a selected wave length range, regardless of whether or not the wave length has been absorbed.

If the cavity contains the light receivers then these are positioned at the same places as the openings 20a, 20b, . . . 20f.

FIG. 4 is meant to illustrate an alternative embodiment in which a light emitter 4 aims diverging rays of light at a mirror 25 whose surface 25a is bent like a circular line with a centre point 25C.

The reflected beams of light strike a plane mirror surface 26a and are reflected across to a plane mirror surface 27a, which in turn reflects the beams of light to the mirror surface 25a that converges the beams of light at the light receiver 5.

Obviously, the various embodiments shown in FIGS. 1, 3 and 4 give different lengths of direct and indirect measuring paths for the light within the cavity 2.

The gas that is to be analysed is introduced through holes or openings outside the area for the flood of light. Exactly where these are positioned must be answered on a case-by-case basis. In the embodiments shown, outlets or holes are indicated by the references 30 and 31.

FIG. 5 shows an embodiment that exploits the principles for White mirrors.

The gas sensor 1 has been adapted to enable a measurement of a gas sample that is enclosed in a cavity 2.

The gas sensor 1 has the shape of a block 50. Each wall or wall section of the cavity 2 exhibits highly reflective properties for light.

Said cavity 2 contains means 51, in this case an opening for incoming diverging light, and means 52, in this case an opening 52 for exiting converging light.

Significant for the present invention is that said cavity 2 in block 50 must contain opposing mirror-related surface sections, such as surface sections 55a, 56a, and 57a, where the surface sections are designed and coordinated so that incoming rays of light 60 are arranged to pass a predetermined number of times—without indirect reflection in the x-z plane, but with indirect reflection in the x-y plane— across said cavity 2 in the x-z plane, thereby providing, in spite of the miniaturisation, a given measuring path before the reflected converging light 61 is aimed to pass through said opening 52 for exiting light.

Also significant for the present invention is that the cavity 2 is formed by two plane light-reflecting surfaces, placed close together, facing one another, parallel in the x-z plane. One surface, in the block 50 is designated 2a. The other surface 2b has the shape of a disk (not pictured).

Said surfaces 2a, 2b are positioned very close to one another, with the distance between them adjusted to the size of the cross-section for the thermal light area for the light emitter 4. In practice, this distance should equal the surface of the light source, which is equal to, or greater than, the surface of the detector.

Further, according to the embodiment of the invention shown in FIG. 5, said opposing surface sections 55a, 56a and 57a are given a slightly bent circular shape.

Part, if not all, of a surface section 57a is processed to exhibit a grid shape, thereby creating an internal grid spectrometer in the block 50.

However, there is no reason why the receiver 5 may not make up, or comprise, a grid spectrometer of this kind.

The invention also shows that the incoming rays of light 60 are produced by a sending organ 4, which has the shape of a lamp with a narrow frequency range.

The exiting rays of light 61 are received by a light detector 5 with a circuit 10 for analysing the absorption spectrum, which is treated in a unit 11, and presented using known methods, via a cable 12, on a display.

The present invention strongly proposes that the block 50 be designed according to the principles used for producing compact disks, with a thickness in the order of 0.3 mm.

According to FIG. 5, the embodiment shows that said opposing surface sections 55a, 56a and 57a are positioned according to the principles for a White mirror.

FIG. 5 illustrates that the opposing surface sections 55a, 56a, 57a and a plane surface 2a are shaped out of a block section 50, whereas the opposing plane surface 2b is shaped as a disk.

Said opposing surface sections and said two plane surfaces are coated with gold. The incoming rays of light 60 are chosen to be within the frequency range for infrared light.

Said gas sample is introduced into the cavity by means of holes 30 and 31. The gas can be introduced via a pump (not pictured), or by diffusion in the cavity.

According to FIG. 5, the embodiment also shows that the mirror surface 55a of the mirror 55 has its circular centre 55C in the mirror surface 56a of the mirror 56, and that the diverging rays of light 60 are directly reflected, converging from the mirror surface 55a, to appear as a point 60' on the mirror surface 56a.

The point 60' is projected, divergently, to the mirror surface 57a of the mirror 57, and is directly reflected, convergently, back to the mirror surface 56a as a point 61, situated the same distance from the point of focus 57C as point 60', but on the other side of the point of focus 57C.

Point 61 is then directly reflected to the mirror surface 55a and reflected again, convergently, as a point 62 on the mirror surface 56a.

Thereafter, point 62 is directly reflected, divergently, in the mirror surface 57a, which directly reflects the beams of light 561 causing them to converge at the light detector 5.

From this description we see that the mirror surface 56a could easily be broken up to have only point-related (60', 61, 62) reflective properties. The areas in between these points could server as gas inlets and outlets (30, 31).

Figure 6:
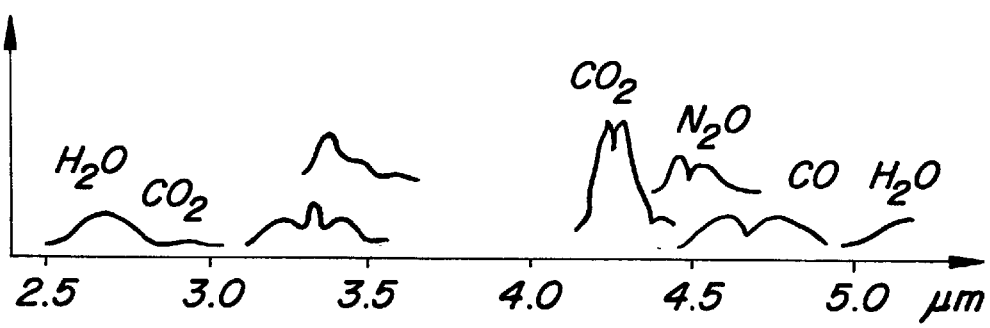
FIG. 6 shows the absorption characteristics of various gases.

FIG. 6 shows the known absorption tendencies of various gases at different wave lengths, as well as the absorption tendencies of certain gases within specific ranges of wave lengths.

It is possible, within the scope of the invention, to produce a gas cell that is inexpensive, preferably from a plastic material that contains recesses for enclosing the light emitters and the light receiver.

If a ceramic material were used to produce the gas cell, then this same material could also be used to form the required electronic circuit for the gas sensor.

We should note in particular that since the light receiver 5 will be able to receive beams of light with different measuring paths, a centrally positioned image 560' from the directly reflected beams of light, and adjacent images 561, 561', as well as 562, 562', and so forth, with increasing measuring paths that correspond to the distance from the centrally positioned image 560', it will be possible, using the same design for the cavity 2, to choose any given measuring path. The measuring path is increased by an increasing diverging angle for the incoming light; for example, 45° to 60°.

If we analyse the received light spectrum for several gases, then as a reference, it is significant that we analyse the intensity of light for wave lengths without absorption as well, thereby providing compensation for changes in the lamp used.

The analysed light intensity can be written according to the following formula:

$$I = I_0 \cdot e^{-s \cdot c \cdot l}$$

where $I_0$ = intensity before absorption;

s = the absorption cross-section;

c = the concentration;

l = the length of the optical measuring path.

By means of the proposed embodiments, in particular the embodiment shown in FIG. 5, it is possible to analyse the intensity of light for a chosen wave length, given a first predetermined optical length, such as in point 560', and a second predetermined optical length, such as in point 562, whereby, through calculation, the value "c" can be determined without consideration for the value Io.

Thus, the same wave length can be used for different measuring paths, thereby establishing a reference while using the same optical filter with the same optical properties.

Obviously, the invention is not restricted to the exemplifying embodiments described above. Instead, modifications can be made within the scope of the inventive thought defined in the following Claims.

I claim:

1. A gas sensor, designed to enable a measurement of a gas sample that is enclosed in a cavity (2), having the shape of a block; the wall or wall sections of the cavity exhibiting highly-reflective properties for light; said cavity containing means (51) for incoming rays of light (60), where said rays of light are arranged to pass reflected across said cavity (2), thereby forming an optical measuring path before the reflected beams of light are aimed towards means (52) for exiting rays of light, characterised in that said cavity (2) exhibits opposing surface sections (2a, 2b) that are designed and coordinated so close together that incoming rays of light (60) are arranged to pass in a plane—without reflecting, or without appreciably reflecting—across said cavity (2) to a concave mirror surface (55a, 56a, 57a) that is oriented in a right angle to the plane and that reflected beams of light are converging at said means (52) for exiting rays of light.

2. According to claim 1, a gas sensor characterised in that the cavity (2) is formed with two light-reflective surfaces (2a, 2b), placed close together, facing one another in parallel planes.

3. According to claim 1, a gas sensor characterised in that the shape of said opposing surface sections (2a, 2b) is slightly bent.

4. According to claim 3, a gas sensor characterised in that at least part of a surface section has been processed to present the shape of a grid.

5. According to claim 1, a gas sensor characterised in that the incoming rays of light (60) are produced by a light emitter with a narrow frequency range.

6. According to claim 1, a gas sensor characterised in that the exiting rays of light are received by a light detector with a circuit for analysing the current absorption spectrum.

7. According to claim 1, a gas sensor characterised in that the block is formed according to the principles that are used for making compact disks.

8. According to claim 1, a gas sensor characterised in that said opposing surface sections (55, 56 and 57) are oriented according to the principles for a White mirror.

9. According to claim 1, a gas sensor characterised in that the opposing surface sections and one plane surface (2a) are formed in of a block, whereas the opposite plane surface (2b) is formed into a disk.

10. According to claim 1, a gas sensor characterised in that said opposing surface section and said two plane surfaces are coated with gold, and that the frequency of the incoming light (60) is chosen to be in the range for infrared light.

11. According to claim 1, a gas sensor characterised in that said gas sample is arranged to be pumped through the cavity (2) by means of a pump.

12. According to claim 1, a gas sensor characterised in that said gas sample is arranged to diffuse into the cavity (2).

13. According to claim 1, a gas sensor characterised in that the reflected rays of light within the cavity (2) are converging and diverging.

14. According to claim 1, a gas sensor characterised in that the cavity is formed in a plastic or silicon disk.

15. According to claim 1, a gas sensor characterised in that a light receiver (5) is designed to receive beams of light of a given wave length with one of several accessible lengths of measurement.

16. According to claim 1, a gas sensor characterised in that one and the same wave length can be assessed for different lengths of measurement, thereby establishing a reference.

17. According to claim 2, a gas sensor characterised in that the shape of said opposing surface sections (2a, 2b) is slightly bent.

18. According to claim 17, a gas sensor characterised in that at least part of a surface section has been processed to present the shape of a grid.

* * * * *